United States Patent [19]

Drent

[11] Patent Number: 4,634,793

[45] Date of Patent: Jan. 6, 1987

[54] PROCESS FOR THE DIMERIZATION OF OLEFINS

[75] Inventor: Eit Drent, Amsterdam, Netherlands

[73] Assignee: Shell Oil Company, Houston, Tex.

[21] Appl. No.: 783,712

[22] Filed: Oct. 3, 1985

Related U.S. Application Data

[63] Continuation-in-part of Ser. No. 754,882, Jul. 15, 1985, abandoned.

[30] Foreign Application Priority Data

Nov. 9, 1984 [GB] United Kingdom ............... 8428347

[51] Int. Cl.$^4$ ................................................ C07C 2/02
[52] U.S. Cl. ................................... 560/243; 560/103; 560/202; 562/590; 585/511; 585/514; 585/527; 585/531
[58] Field of Search ............... 560/243; 568/695, 697, 568/900; 585/365, 511, 514, 527, 531

[56] References Cited

U.S. PATENT DOCUMENTS

| 3,711,534 | 1/1973 | Manyik | 560/244 |
| 3,798,260 | 3/1974 | Hattri | 560/244 |
| 4,518,814 | 5/1985 | Knudsen | 585/527 |
| 4,528,415 | 7/1985 | Knudsen | 585/527 |
| 4,528,416 | 7/1985 | Lutz | 585/527 |

Primary Examiner—Michael L. Shippen

[57] ABSTRACT

A process for the dimerization in the liquid phase of an aliphatic mono-olefin having 2 to about 12 carbon atoms with a catalytic system formed by combining, in the presence of water, an alcohol or a carboxylic acid,
 a. a palladium compound,
 b. a chelate ligand having as coordinating atoms at least two Group Va atoms which are connected through a chain comprising 2 to about 6 carbon atoms, and
 c. a compound containing an anion of an acid, except hydrohalogenic acids.

22 Claims, No Drawings

PROCESS FOR THE DIMERIZATION OF OLEFINS

This is a continuation-in-part of co-pending application Ser. No. 754,882, filed July 15, 1985, now abandoned.

FIELD OF THE INVENTION

The present invention relates to a process for the dimerization of low molecular weight aliphatic mono-olefins by using a catalytic system containing palladium.

BACKGROUND OF THE INVENTION

It is known that in the palladium catalyzed dimerization of low molecular weight aliphatic mono-olefins a catalytic system can be used, which is formed by combining a palladium halide with an organoaluminum halide and preferably with a monodentate phosphine, arsine or stibine (cf. UK Patent specification No. 1,153,519). It is also known to dimerize propene in the presence of a catalytic system formed by combining pentanedionatopalladium with ethylaluminum dichloride and an organic monodentate phosphine or phosphite (cf. Angew. Chem. Int. Ed. 14, 104–105 (1975).

Because of the presence of organoaluminum halides in the catalytic systems the above dimerization reactions should be carried out under strictly anhydrous conditions.

Further, it is known how to dimerize ethene with a catalytic system formed by combining tetrakis(acetonitrile)palladium ditetrafluoroborate with a monodentate phosphine ligand (cf. J. Am. Chem. Soc. 103, 4627–4629 (1981) and 104, 3520–3522 (1982). Once again, this dimerization has to be carried out under strictly anhydrous conditions (cf. Transition metal catalyzed polymerisations; Alkenes and Dienes, Part A, Edited by R. P. Quirk, 1983, pp. 341–354).

SUMMARY OF THE INVENTION

The present invention relates to a process for the dimerization in the liquid phase of an aliphatic mono-olefin having 2 to about 12 carbon atoms with a catalytic system formed by combining, in the presence of water, an alcohol or a carboxylic acid, a. a palladium compound,
b. a chelate ligand comprising an organic compound containing as coordinating atoms at least two atoms of Group Va of the Periodic System of Elements which are connected through a chain comprising 2 to about 6 carbon atoms, and
c. a compound containing an anion of an acid with a pKa of less than 2, with the exception of hydrohalogenic acids.

It is an advantage of the process of the invention that the catalytic systems used therein do not require anhydrous reaction conditions. In addition high reaction rates can be achieved while maintaining an attractive reaction selectivity. The selectivity to dimers is defined as the molar percentage of dimers in the product formed.

DESCRIPTION OF THE PREFERRED EMBODIMENTS

Aliphatic mono-olefins having 2 to about 12 carbon atoms which can be used in the process for dimerization according to the invention are linear or branched alkenes or cycloalkenes, such as for example ethene, propene, butene-1, butene-2, the isomeric pentenes, hexenes, octenes and dodecenes, cyclopentene, cyclooctene and cyclododecene. Examples of other aliphatic mono-olefins are substituted alkenes such as allyl alcohol, acrylic acid and alkylesters of acrylic acid. The preferred olefins are ethene, propene, and butene-1.

It is to be pointed out that the "dimerization" as it is employed herein, refers to the reaction of two identical olefins as well as to the reaction of two different olefins.

According to the invention, both homogeneous and heterogeneous catalytic systems can be used. The use of homogeneous catalytic systems is preferred.

Palladium compounds which can be used in the catalytic system of the invention therefore preferably comprise palladium compounds which are soluble in the reaction medium or form in situ soluble compounds therein. Examples of suitable palladium compounds are palladium nitrate, palladium sulfate, palladium halides and palladium carboxylates, preferably carboxylates of carboxylic acids having not more than about 12 carbon atoms per molecule. Palladium carboxylates, in particular palladium acetate, are preferably used.

Further examples of suitable palladium compounds are palladium complexes such as bis(2,4-pentanedionato)palladium, bis(picolinato)palladiium, tetrakis(triphenylphosphine)palladium, tetrakisacetonitrile palladium tetrafluorobate, bis(tri-o-tolylphosphine)palladium acetate, bis(tri-phenylphosphine)palladium sulfate, palladium olefin complexes for instance di-$\mu$-chlorodichlorobis(ethlyene)dipalladium([Pd.C$_2$H$_4$.Cl$_2$]$_2$), and di-$\mu$-chlorodichlorobis(propylene)-dipalladium([Pd.C$_3$H$_6$.Cl$_2$]$_2$), and palladium-hydride complexes. The quantity of the palladium compound used may vary within wide ranges and is generally in the range between about $10^{-6}$ and about $10^{-1}$ mol palladium compound per mol olefin starting material. A range between about $10^{-5}$ and about $10^{-2}$ mol palladium compound is preferred.

The chelate ligand which may be used in the catalytic system according to the invention comprises an organic compound containing as coordinating atoms at least two atoms of Group Va of the Periodic System of Elements which are connected through a chain comprising 2 to about 6 carbon atoms.

Suitable compounds may be compounds containing two nitrogen atoms which are connected through a chain comprising 2 carbon atoms such as 1 2-ethanediamine compounds for example N,N,N',N'-tetramethyl-1,2-ethanediamine, N,N,N',N'-tetraethyl-2,2-ethanediamine and N,N,N',N'-tetraphenyl-1,2-ethanediamine, heterocyclic diamines for example 1,4-diphenylpiperazine, 1,4-dimethyl-1,4-dihydropyrazine, and compounds containing in the molecule a group of the formula

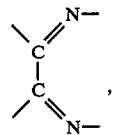

for example N,N'-1,2-ethanediylidene bisbenzeneamine, N,N'-1,2-ethanediylidenebis[4-chlorobenzeneamine], N,N'-1,2-ethanediylidenebis-[4-methoxybenzeneamine], N-substituted derivatives of 2-pyridinemethanimine, 2,2'-bipyridyl, 4,4'-dimethyl-2,2'-dipyridyl, 4,4'-dichloro-2,2'-bipyridyl, 4,4'-dimethoxy-2,2'-bipyridyl, 1,10-phenanthroline, 5-chloro-1,10-phenanthroline 4,7-diphenyl-1,10-phenanthroline, 4,7-dimethyl-1,10-phenanthroline, 2,9-dichloro-1,10-phenanthroline, 1,10-phenanthroline, 1,10-phenanthroline-5-sulfonic acid, 4,7-diphenyl-1,10-phenanthrolinedisulfonic acid, and 3,5-cyclohexadiene-1,2-diimine.

Other suitable compounds may be compounds containing two phosphorus atoms, or two arsenic atoms or optionally a phosphorus atom or an arsenic atom in combination with a nitrogen atom which are connected through a chain comprising 2 carbon atoms such as, for example, 1,2-ethanediylbisdiphenylphosphine, 1,2-ethenediylbisphenylphosphine, 1,2-ethynediylbisdiphenylphosphine, 1,2-ethanediylbisdi(trifluoromethyl)phosphine, 1,2-phenylenebisdiphenylphosphine, 1,2-tetrafluorocyclobutenediylbisdiphenylphosphine, 1,2-hexafluorocyclopentenediylbisdiphenylphosphine, 1,2-octafluorocyclohexenediylbisdiphenylphosphine, 1,4-diphenyl-1,4-diphosphacyclohexane, bis(o-diphenylphosphinophenyl)phenylphosphine, tris-(o-diphenylphosphinophenyl)phosphine, 1,2-phenylenebisdimethylarsine, 1,2-ethanediylbisdiphenylarsine, 1-dimethylamino-2-phenyldiethylphosphine, 8-dimethylarsinoquinoline, 10-methyl-5,10-dihydrophenarsazine, 1,2-tetrafluorophenylenebisdimethylarsine.

Further suitable compounds may be compounds containing at least two nitrogen atoms, phosphorus atoms or arsenic atoms connected through a chain comprising 3-5 carbon atoms such as for example, N,N,N',N'-tetramethyl-1,3-propanediamine, N,N,N'N'-tetramethyl-1,4-butanediamine, 1,3-propanediylbisdiphenylphosphine, 1,4-butanediylbisdiphenylphosphine, bis(bis-3-dimethylarsinopropyl)arsine, tetrakis-(3-dimethylarsinopropyl)o-phenylenediarsine.

The compounds preferably used in the catalytic system of the invention are 1,10-phenanthroline(o-phenanthroline) and the derivatives thereof, 2,2'-bipyridyl and the derivatives thereof and bisdiphenylphosphine compounds in which the two phosphorus atoms are connected through a chain comprising 2 or 3 carbon atoms. The phenyl groups in the bisdiphenylphosphine compounds may be either substituted or unsubstituted.

The quantity of chelate ligands used in the catalytic system is at least 0.1 mol ligand per gram atom palladium and preferably varies between about 1 and 25 mol ligand per gram atom palladium.

The catalytic system used in the process of the invention is further formed by a compound containing an anion of an acid with a pKa of less than 2 except hydrohalogenic acids. The anion is preferably a noncoordinating anion, by which is meant that little or no covalent interaction takes place between the palladium and the anion (cf. UK Patent Application No. 2,058,074). Typical examples of such anions are $PF_6^-$, $SbF_6^-$, $BF_4^-$ and $ClO_4^-$.

The anion-containing compound may be a salt or a metal complex compound containing an anion of the acid or may be the acid itself. The acid preferably has a pKa of less than 3 and, more preferably, less than 2, measured in an aqueous solution at a temperature of 18° C.

Preferred compounds are those containing anions of, for example, sulfonic acids and acids that can be formed, possibly in situ, by interacting a Lewis acid such as, for example, $BF_3$, $AsF_5$, $SbF_5$, $PF_5$, $TaF_5$ or $NbF_5$ with a Broensted acid such as, for example, a hydrohalogenic acid, in particular HF, fluorosulfonic acid, phosphoric acid or sulfuric acid. Specific examples of acids of the latter type are fluorosilicic acid, $HBF_4$, $HPF_6$, and $HSbF_6$. Examples of usable sulfonic acids are fluorosulfonic acid and chlorosulfonic acid and the hereinafter specified sulfonic acids.

A preferred group of compounds are compounds containing anions of acids having the general formula

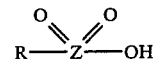

in which Z represents sulfur or chlorine and, if Z is chlorine, R represents oxygen and, if Z is sulfur, R represents an OH group or an optionally substituted hydrocarbon group.

When the hereinbefore-stated anion-containing compounds are used in the process according to the invention, the anions of the compounds can be considered to be non-coordinating.

The optionally substituted hydrocarbon group represented by R is preferably an alkyl, aryl, aralkyl or alkaryl group having 1 to about 30, in particular 1 to about 14, carbon atoms. The hydrocarbon group may, for example, be substituted with the halogen atoms, in particular fluorine atoms. Examples of suitable acids of the general formula I are perchloric acid, sulfuric acid, 2-hydroxypropane-2-sulfonic acid, benzenesulfonic acid, 1-and-2-naphthalenesulfonic acid, p-toluenesulfonic acid and trifluoromethanesulfonic acid, the last two acids being the most preferred.

According to another embodiment of the present invention, the catalytic system is formed by using a compound containing an anion of a carboxylic acid as component (c). Examples of suitable carboxylic acids are formic acid, acetic acid, monochloroacetic acid, dichloroacetic acid, trichloroacetic acid and trifluoroacetic acid, the latter acid being the most preferred.

The anion-containing compound is preferably used in the form of the acid itself. However, under certain conditions it is possible to use salts containing an anion of the acid, which can be exchanged with the anion of the palladium compound used. For example, $AgBF_4$, $AgSbF_6$ or As-p-toluene sulfonate can be used when the palladium compound is palladium chloride or a palladium complex compound containing chloride anions.

The compound containing an anion of the acid having a pKa of less than 2 is preferably used in a quantity of about 0.01 to about 150 and in particular about 1 to about 100 equivalents per gram atom palladium.

It will be appreciated that when the catalytic system of the invention is formed by combining in situ a palladium compound, a chelate ligand and a compound containing an anion of the acid a palladium complex compound with catalytic activity may be formed in the reaction mixture. An example of such a compound is palladium bis(1,10-phenanthroline)diperchlorate or ditosylate. The use of such a palladium complex compound when prepared separately as catalytic system is within the scope of the present invention.

In the process of the invention the catalytic system is used in the presence of the protic compounds water, alcohol, or carboxylic acid. The alcohols or carboxylic acids may be aliphatic, cycloaliphatic or aromatic and may be substituted with one or more substituents for example alkoxy, cyano ester groups or halogen atoms. The alcohols or carboxylic acids preferably contain not more than about 20 carbon atoms. Example of suitably alcohols are methanol, ethanol, propanol, isobutanol, tert-butanol, stearyl alcohol, benzyl alcohol, cyclohexanol, allyl alcohol, chlorocapryl alcohol, ethylene glycol, propanediol-(1,2), butanediol-(1,4), glycerol, polyethylene glycol, hexanediol-(1,6), phenol, cresol. Special preference is given to alcohols having 1 to about 10 carbon atoms per molecule.

Examples of suitable carboxylic acids are acetic acid, propionic acid, butyric acid, caproic acid, trimethylacetic acid, benzoic acid, caprylic acid, succinic acid, adipic acid and hydroxycaproic acid.

The amount of water, alcohol or carboxylic acid used in the reaction mixture may be any amount that activates the catalytic system. Conveniently, such amounts can be used that water serves as co-solvent and the alcohol or carboxylic acid as solvent or co-solvent.

The process according to the invention is carried out in the liquid phase which may comprise a liquid mixture of the olefin, the catalytic system, reaction products, water, an alcohol or a carboxylic acid and preferably a solvent or co-solvent.

As stated hereinabove, water, alcohols or carboxylic acids can be used as solvent or co-solvent. Further examples of solvents and co-solvents are hydrocarbons, in particular aromatic hydrocarbons such as hexane, benzene or toluene, halogenated hydrocarbons such as chloroform, chlorobenene or perfluoroalkanes, ketones such as acetone, diethyl ketone or methylisobutyl ketone, ethers such as tetrahydrofuran, dimethylether of diethylene glycol(diglyme), methyl-t-butyl ether or 1,4-dioxane, sulphones such as dimethyl sulphone, methylbutyl sulphone, sulpholane and sulphoxides such as dimethylsulphoxide or diethylsulphoxide.

The liquid phase may comprise a two-phase liquid system. For example, when ethene or propene is dimerized using a diol as solvent, the dimerization product may form a separate layer which can be easily separated from diol solvent containing the catalytic system.

The process according to the present invention can be carried out at temperatures of up to about 200° C. and preferably in the range between about 20° C. and about 135° C. The pressure preferably lies between about 1 and about 100, in particular between about 20 and about 75, bar gauge.

The process according to the invention can be carried out batchwise, semi-continuously or continuously. The reaction time may vary in relation to the temperature used, between about 0.5 and about 20 hours. The process according to the invention is hereinafter illustrated on the basis of practical examples, which are provided for illustrative purposes and are not to be construed as limiting the invention.

EXAMPLE 1

A 300 ml magnetically stirred Hastelloy C autoclave ("Hastelloy" is a trade mark) was charged with 50 ml methanol and a catalytic system as described below. The autoclave was flushed with ethene, filled with ethene at a pressure of 40 bar, sealed and heated to a temperature as indicated in Table I. After a reaction time as indicated in Table I the contents of the autoclave were analyzed by gas/liquid chromatography.

The conversion of ethene to products, (dimers, trimers, etc.) was calculated as mols of ethene per gram atom palladium per hour. The selectivity to the dimer butenes is given as %mol dimer in the products formed.

The results of the experiments 1–10 are mentioned in Table I.

EXPERIMENT 1

As catalytic systems were added 0.1 mmol of palladium acetate, 0.15 mmol of 1,3-propanediylbisdiphenylphosphine and 2 mmol of p-toluenesulfonic acid.

EXPERIMENT 2

As catalytic system was added a composition of palladium complex compounds containing 0.1 mgram atom palladium. The composition was prepared as follows: Palladium acetate was dissolved in methanol and 3 mol of p-toluenesulfonic acid per gram atom palladium and 1.5 mol of 1,3-propanediylbisdiphenylphosphine per gram atom palladium were added. The resulting precipitate was isolated by filtration and washed with methanol.

EXPERIMENT 3

As catalytic system was added a composition prepared analogously to the composition of experiment 2 except that 3 mol of HCl (11N) was used instead of 3 mol of p-toluenesulfonic acid.

EXPERIMENT 4

As catalytic system were added 0.1 mmol of palladium acetate, 2 mmol of 2,2'-bipyridine and 1 mmol of p-toluenesulfonic acid.

EXPERIMENT 5

As catalytic system were added 0.1 mmol of palladium acetate, 2 mmol of 1,10-phenanthroline and 1 mmol of p-toluenesulfonic acid.

EXPERIMENT 6

As catalytic system was added a composition prepared analogously to the composition of experiment 2 except that 2 mol of 1,10-phenanthroline was used instead of 1.5 mol of 1,3-propanediylbisdiphenylphosphine.

EXPERIMENT 7

The catalytic system was formed by combining 0.5 mmol palladium acetate, 1 mmol 1,10-phenanthroline and 10 mmol acetic acid.

EXPERIMENT 8

The catalytic system was formed by combining 0.5 mmol palladium acetate, 1 mmol 1,10-phenanthroline and 2 mmol monochloroacetic acid.

EXPERIMENT 9

The catalytic system was formed by combining 0.5 mmol palladium acetate, 1 mmol 1,10-phenanthroline and 2 mmol dichloroacetic acid.

EXPERIMENT 10

The catalytic system was formed by comining 0.5 mmol palladium acetate, 1 mmol 1,10-phenanthroline and 2 mmol trifluoroacetic acid. The selectivities to trimers and tetramers were 25% and 2%, respectively.

TABLE I

| Exp. No. | Temp, °C. | Time, h | Conversion mol/gr. at Ph/h | Selectivity, % mol |
|---|---|---|---|---|
| 1 | 95 | 0.5 | 6000 | 98 |
| 2 | 95 | 0.5 | 6000 | 98 |
| 3 | 115 | 5 | 70 | 100 |
| 4 | 75 | 0.5 | 8000 | 85 |
| 5 | 90 | 1 | 5000 | 93 |

TABLE I-continued

| Exp. No. | Temp, °C. | Time, h | Conversion mol/gr. at Ph/h | Selectivity, % mol |
|---|---|---|---|---|
| 6 | 95 | 2 | 2400 | 95 |
| 7 | 75 | 5 | 120 | — |
| 8 | 75 | 5 | 200 | — |
| 9 | 75 | 5 | 300 | — |
| 10 | 75 | 0.16 | 5600 | 73 |

Experiment 3 is not according to the invention and shows that a high conversion is not achieved in the presence of chloride anions.

EXAMPLE 2

A 300 ml magnetically stirred Hastelloy C autoclave ("Hastelloy" is a trade mark) was charged with 50 ml diglyme, 5 ml water and as catalytic system 0.1 mmol of palladium acetate, 2 mmol of 2,2'-bipyridyl and 2 mmol of p-toluenesulfonic acid. The autoclave was flushed with ethene, filled with ethene at a pressure of 40 bar, sealed and heated at 90° C. After a reaction time of 1 hour the contents of the autoclave were analyzed by gas/liquid chromatography.

The conversion of ethene to dimers and trimers was calculated as 2800 mol of ethene per gram atom palladium per hour. Butenes were present in an amount of 93%mol in the product.

For comparison this experiment was repeated except that no water was present and that was heated at 120° C. during 5 hours. On analysis only traces of butenes were found, showing that the catalytic system effects dimerization in the presence of water protic compound.

EXAMPLE 3

A 300 ml magnetically stirred Hastelloy C autoclave ("Hastelloy" is a trade mark) was charged with 35 ml phenol and as catalytic system 0.1 mmol of palladium acetate, 4 mmol of 2,2'-bipyridine and 4 mmol of p-toluenesulfonic acid. The autoclave was flushed with ethene and filled with ethene at a pressure of 40 bar, sealed and heated to 80° C. After a reaction time of 5 hours the contents of the autoclave were analyzed by gas/liquid chromatography.

The conversion of ethene to dimers and trimers was calculated as 800 mol of ethene per gram atom palladium per hour. Butenes were present in an amount of 90%mol in the product.

EXAMPLE 4

A 300 ml magnetically stirred Hastelloy C autoclave ("Hastelloy" is a trade mark) was charged with 50 ml acetic acid and as catalytic system 0.1 mmol of palladium acetate, 0.15 mmol of 1,3-propanediylbisdiphenylphosphine and 2 mol of trifluoromethanesulfonic acid. The autoclave was flushed with ethene and filled with ethene at a pressure of 40 bar, sealed and heated to 135° C. After a reaction time of 5 hours the contents of the autoclave were analyzed by gas/liquid chromatography.

The conversion of ethene to dimer products (butene 40%mol and sec.butyl acetate 60%mol) was calculated as 500 mol of ethene per gram atom palladium per hour. The selectivity to dimer products was 100%mol.

EXAMPLE 5

A 300 ml magnetically stirred Hastelloy C autoclave ("Hastelloy" is a trade mark) was charged with a solvent and as catalytic system palladium acetate, a bidentate ligand and an acid with a pKa<2. The autoclave was flushed with propene, filled with propene in the liquid phase at 30 bar in a quantity of 50 ml, sealed and heated to a certain temperature. After a certain reaction time the contents of the autoclave were analyzed by gas/liquid chromatography.

The conversion of propene to products was calculated as mol of propene per gram atom palladium per hour. The selectivity to the dimers is given as %mol of dimer in the products formed. The linearity of the dimer products is determined by NMR and is given as %mol of linear hexenes in the dimer products.

Data and results of the experiments 1-7 carried out according to the above are mentioned in Table II.

TABLE II

| Exp. No. | Palladium acetate mmol | Bidentate ligand (mmol) | Acid pKa < 2 (mmol) | Solvent (ml) | Reaction time h | Temp. °C. | Conversion, m/g at Pd/h | Selectivity % mol | Linearity % mol |
|---|---|---|---|---|---|---|---|---|---|
| 1 | 0.2 | 2,2'bipyridine (4) | p-toluenesulfonic acid (6) | methanol (50) | 2 | 85 | 1050 | 98 | 65 |
| 2 | 0.5 | 1,10-phenanthroline (1) | p-toluenesulfonic acid (1.5) | butanediol —(1.4) (50) | 1 | 75 | 1250 | 94 | 60 |
| 3 | 0.5 | 2,2'bipyridine (1) (1.5) | p-toluenesulfonic acid (1.5) | ethylene glycol (50) | 1 | 75 | 1100 | 95 | 58 |
| 4 | 0.5 | 1,10-phenanthroline (1) | sulfuric acid (1.5) | diethylene glycol (50) | 1 | 70 | 1050 | >95 | 60 |
| 5 | 0.5 | 1,10-phenanthroline (1) | HBF$_4$ (3) | diethylene glycol (50) | ½ | 70 | 4000 | >95 | 59 |
| 6 | 0.5 | 4,7-diphenyl-1,10-phenanthroline (1) | trifluoromethanesulfonic acid (1.5) | ethylene glycol (50) | ½ | 75 | 1800 | >95 | 60 |
| 7 | 0.5 | 5-chloro-1,10-phenanthroline (1) | naphthalenesulfonic acid (2) | diethylene glycol (50) | 1 | 75 | 930 | >95 | 59 |

EXAMPLE 6

A 300 ml magnetically stirred Hastelloy C autoclave ("Hastelloy" is a trade mark) was charged with 50 ml butanediol-(1,4) and as catalytic system 0.5 mmol of palladium acetate, 1 mmol of 1,10-phenanthroline and 1.5 mmol p-toluenesulfonic acid. The autoclave was flushed with butene-1 and filled with butene-1 in the liquid phase at 30 bar in a quantity of 60 ml and heated to 75° C. After a reaction time of 5 hours the contents of the autoclave were analyzed by gas/liquid chromatography.

The conversion of butene-1 to dimers was calculated as 30 mol of butene-1 per gram palladium per hour. Dimers were the only products.

EXAMPLE 7

A 300 ml magnetically stirred Hastelloy C autoclave ("Hastelloy" is a trade mark) was charged with 50 ml methanol and as catalytic system 1 mmol of palladium acetate, 2 mmol of 2,2-bipyridine and 2.5 mmol p-toluensulfonic acid. The autoclave was flushed with propene and filled with propene and butene-1 in the liquid phase at 30 bar in a quantity of 50 ml and 60 ml, respectively, and heated to 65° C.

The conversion to dimer product was calculated as 800 mol of propene and butene per gram atom palladium per hour. The selectivity to dimers was 100%mol. The composition of the dimer products was hexenes 69%mol, heptenes 28 %mol and octenes 3%mol.

I claim:

1. A process for the dimerization in the liquid phase of an aliphatic mono-olefin having 2 to 12 carbon atoms which process comprises contacting said olefins with a catalytic system formed by combining, in the presence of water, an alcohol, or a carboxylic acid,
   a. a palladium compound,
   b. a chelate ligand comprising an organic compound containing as coordinating atoms at least two atoms of Group Va of the Periodic System of Elements which are connected through a chain comprising 2 to 6 carbon atoms, and
   c. a compound containing an anion of an acid with the exception of hydrohalogenic acids.

2. The process of claim 1, wherein the acid in (c) has a pKa of less than 3, measured in aqueous solution at a temperature of 18° C.

3. The process of claim 2, wherein the acid has a pKa of less than 2.

4. The process of claim 1, wherein as anion a non-coordinating anion is used.

5. The process of claim 1, wherein the compound containing an anion of an acid contains the anion of an acid of the general formula I

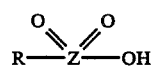

wherein Z represents sulfur or chlorine and, if Z is chlorine, R represents oxygen and, if Z is sulfur, R represents an OH group or hydrocarbon group.

6. The process of claim 3, wherein the hydrocarbon group R is an alkyl, aryl, aralkyl or alkaryl group having 1 to about 30 carbon atoms.

7. The process of claim 3, wherein the anion of an acid of the general formula I is an anion of p-toluenesulfonic acid.

8. The process of claim 1, wherein the acid in (c) is trifluoroacetic acid.

9. The process of claim 1, wherein the compound containing an anion of the acid is used in the form of the acid itself.

10. The process of claim 1, wherein the chelate ligand comprises a compound containing as coordinating atoms 2 nitrogen atoms connected through a chain comprising 2 carbon atoms.

11. The process of claim 10, wherein the chelate ligand comprises a compound containing in the molecule a group of the formula

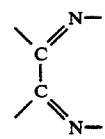

12. The process of claim 10, wherein the chelate ligand comprises 1,10-phenanthroline and the N-substituted derivatives thereof.

13. The process of claim 10, wherein the chelate ligand comprises 2,2'-bipyridyl and the N-substituted derivatives thereof.

14. The process of claim 1, wherein the chelate ligand comprises a compound containing as coordinating atoms 2 phosphorus atoms connected through a chain comprising 2 or 3 carbon atoms.

15. The process of claim 14, wherein the chelate ligand comprises bisdiphenylphosphine compounds in which the phenyl groups are substituted.

16. The process of claim 14, wherein the chelate ligand comprises 1,3-propanediylbisdiphenylphosphine.

17. The process of claim 1, wherein the quantity of the chelate ligand varies between about 1 and about 25 mol ligand per gram atom palladium.

18. The process of claim 1, wherein the compound containing an anion of an acid is used in a quantity of about 1-100 equivalents per gram atom palladium.

19. The process of claim 1, wherein water is used as a co-solvent.

20. The process of claim 1, wherein an alcohol is used as solvent or co-solvent.

21. The process of claim 1, wherein the process is carried out at a temperature in the range between about 20° C. and about 135° C.

22. The process of claim 14, wherein the chelate ligand comprises bisdiphenylphosphine compounds.

* * * * *